United States Patent [19]

Natsoulis

[11] Patent Number: 5,622,856
[45] Date of Patent: Apr. 22, 1997

[54] HIGH EFFICIENCY HELPER SYSTEM FOR AAV VECTOR PRODUCTION

[75] Inventor: Georges Natsoulis, Berkeley, Calif.

[73] Assignee: Avigen, Alameda, Calif.

[21] Appl. No.: 510,790

[22] Filed: Aug. 3, 1995

[51] Int. Cl.[6] .............................. C12N 5/10; C12N 15/63
[52] U.S. Cl. ...................... 435/325; 435/320.1; 435/366;
435/367; 435/369; 435/348; 435/69.1; 536/23.72
[58] Field of Search ................................. 435/69.1, 172.3,
435/320.1, 240.2; 536/23.72, 24.1; 935/23, 32

[56] References Cited

U.S. PATENT DOCUMENTS

| 5,139,941 | 8/1992 | Muzyczka et al. | 435/172.3 |
| 5,173,414 | 12/1992 | Lebkowski et al. | 435/172.3 |
| 5,436,146 | 7/1995 | Shenk et al. | 435/172.3 |

FOREIGN PATENT DOCUMENTS

| WO95/06743 | 3/1995 | WIPO . |
| WO95/13365 | 5/1995 | WIPO . |
| WO95/13392 | 5/1995 | WIPO . |

OTHER PUBLICATIONS

Jayaram, "Two-micrometer Circle Site-specific Recombination: The Minimal Substrate and the Possible Role of Flanking Sequences," *Proc. Natl. Acad. Sci. USA* (1985) 82:5875–5879.

McCarty et al., "Sequences Required for Coordinate Induction of Adeno-Associated Virus p19 and p40 Promoters by Rep Protein," *J. Virol.* (1991) 65(6):2936–2945.

O'Gorman et al., "Recombinase-mediated Gene Activation and Site-specific Integration in Mammalian Cells," *Science* (1991) 251:1351–1355.

Samulski et al., "Helper-free Stocks of Recombinant Adeno-associated Viruses: Normal Integration Does Not Require Viral Gene Expression," *J. Virol.* (1989) 63(9):3822–3828.

Primary Examiner—David Guzo
Assistant Examiner—Robert Schwartzman
Attorney, Agent, or Firm—Reed & Robins

[57] ABSTRACT

Novel nucleic acid molecules are provided having adeno-associated virus (AAV) coding regions that are capable of expressing necessary AAV functions to complement an AAV vector in the production of recombinant AAV (rAAV) virions. The molecules feature a nucleotide sequence that is substantially homologous to an AAV p5 promoter region, wherein the p5 promoter region is situated in the molecules in a site that is other than its natural position relative to the AAV rep coding region in the wild-type AAV genome. AAV helper function constructs are also provided, comprising the instant nucleic acid molecules embodied in a replicon that is capable of being transcribed and translated to express complementing AAV helper functions in a suitable host cell. Novel AAV packaging cells and AAV producer cells are provided, which contain the AAV helper constructs of the invention, and methods of producing enhanced levels of rAAV virions using the AAV helper constructs of the invention are also provided. Methods are also provided for producing rAAV virions without the concomitant production of significant levels of wild-type AAV.

35 Claims, 3 Drawing Sheets (59 bp "minimum" FRT site):

GATCAGAAGT TCCTATTCCG AAGTTCCTAT TCTCTAGAAA
GTATAGGAAC TTCTGATCT (76 bp FRT site):

GATCAGAAGT TCCTATTCCG AAGTTCCTAT TCTCTAGAAA
GTATAGGAAC TTCAGAGCGC TTTTGAAGCT CTGATC

FIG. 3

```
  1                                            GGAGG GGTGGAGTCG

16   TGACGTGAAT TACGTCATAG GGTTAGGGAG GTCCTGTATT AGAGGTCACG

66   TGAGTGTTTT GCGACATTTT GCGACACCAT GTGGTCACGC TGGGTATTTA

116   AGCCCGAGTG AGCACGCAGG GTCTCCATTT TGAAGCGGGA GGTTTGAACG

166   CGCAGCCGCC ATGCCGGGGT TTTACGAGAT TGTGATTAAG GTCCCCAGCG

216   ACCTTGACGG GCATCTGCCC GGCATTTCTG ACAGCTTTGT GAACTGGGTG

266   GCCGAGAAGG AATGGGAGTT GCCGCCAGAT TCTGACATGG ATCTGAATCT

316   GATTGAGCAG GCACCCCTGA CCGTGGCCGA GAAG
```

FIGURE 4

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
CTCTAGTGGA TCT                                                                    13
```

( 2 ) INFORMATION FOR SEQ ID NO:2:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
GATCAGAAGT TCCTATTCCG AAGTTCCTAT TCTCTAGAAA GTATAGGAAC TTCTGATCT   59
```

( 2 ) INFORMATION FOR SEQ ID NO:3:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
GATCAGAAGT TCCTATTCCG AAGTTCCTAT TCTCTAGAAA GTATAGGAAC TTCAGAGCGC   60

TTTTGAAGCT CTGATC                                                                  76
```

( 2 ) INFORMATION FOR SEQ ID NO:4:

( i ) SEQUENCE CHARACTERISTICS:
        ( A ) LENGTH: 349 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
GGAGGGGTGG AGTCGTGACG TGAATTACGT CATAGGGTTA GGGAGGTCCT GTATTAGAGG    60

TCACGTGAGT GTTTTGCGAC ATTTTGCGAC ACCATGTGGT CACGCTGGGT ATTTAAGCCC   120
```

| | | | | | | |
|---|---|---|---|---|---|---|
| GAGTGAGCAC | GCAGGGTCTC | CATTTTGAAG | CGGGAGGTTT | GAACGCGCAG | CCGCCATGCC | 180 |
| GGGGTTTTAC | GAGATTGTGA | TTAAGGTCCC | CAGCGACCTT | GACGGGCATC | TGCCCGGCAT | 240 |
| TTCTGACAGC | TTTGTGAACT | GGGTGGCCGA | GAAGGAATGG | GAGTTGCCGC | CAGATTCTGA | 300 |
| CATGGATCTG | AATCTGATTG | AGCAGGCACC | CCTGACCGTG | GCCGAGAAG | | 349 |

HIGH EFFICIENCY HELPER SYSTEM FOR AAV VECTOR PRODUCTION

DESCRIPTION

1. Technical Field

The present invention relates generally to helper function systems for use in adeno-associated virus (AAV) vector production. More specifically, the invention relates to AAV helper function constructs which provide for the expression of essential AAV rep and cap functions necessary for production of AAV virions.

2. Background of the Invention

Gene delivery is a promising method for the treatment of acquired and inherited diseases. A number of viral based systems for gene transfer purposes have been described, such as retroviral systems which are currently the most widely used viral vector systems for this purpose. For descriptions of various retroviral systems, see, e.g., U.S. Pat. No. 5,219,740; Miller and Rosman (1989) *BioTechniques* 7:980–990; Miller, A. D. (1990) *Human Gene Therapy* 1:5–14; Scarpa et al. (1991) *Virology* 180:849–852; Burns et at. (1993) *Proc. Natl. Acad. Sci. USA* 90:8033–8037; and Boris-Lawrie and Temin (1993) *Cur. Opin. Genet. Develop.* 3:102–109.

Adeno-associated virus (AAV) systems have also been used for gene delivery. AAV is a helper-dependent DNA parvovirus which belongs to the genus Dependovirus. AAV requires co-infection with an unrelated helper virus, either adenovirus, a herpesvirus or vaccinia, in order for a productive infection to occur. In the absence of such co-infection, AAV establishes a latent state by insertion of its genome into a host cell chromosome. Subsequent infection by a helper virus rescues the integrated copy which can then replicate to produce infectious viral progeny. AAV has a wide host range and is able to replicate in cells from any species so long as there is also a successful co-infection of such cells with a suitable helper virus. Thus, for example, human AAV will replicate in canine cells co-infected with a canine adenovirus. AAV has not been associated with any human or animal disease and does not appear to alter the biological properties of the host cell upon integration. For a review of AAV, see, e.g., Berns and Bohenzky (1987) *Advances in Virus Research* (Academic Press, Inc.) 32:243–307.

The AAV genome is composed of a linear, single-stranded DNA molecule which contains 4681 bases (Berns and Bohenzky, supra). The genome includes inverted terminal repeats (ITRs) at each end which function in cis as origins of DNA replication and as packaging signals for the virus. The ITRs are approximately 145 bp in length. The internal nonrepeated portion of the genome includes two large open reading frames, known as the AAV rep and cap regions, respectively. These regions code for the viral proteins involved in replication and packaging of the virion. In particular, a family of at least four viral proteins are synthesized from the AAV rep region, Rep 78, Rep 68, Rep 52 and Rep 40, named according to their apparent molecular weight. The AAV cap region encodes at least three proteins, VP1, VP2 and VP3. For a detailed description of the AAV genome, see, e.g., Muzyczka, N. (1992) *Current Topics in Microbiol. and Immunol.* 158:97–129.

The construction of recombinant AAV virions has been described. See, e.g., U.S. Pat. Nos. 5,173,414 and 5,139,941; International Publication Numbers WO 92/01070 (published 23 Jan. 1992) and WO 93/03769 (published 4 Mar. 1993); Lebkowski et al. (1988) *Molec. Cell. Biol.* 8:3988–3996; Vincent et al. (1990) *Vaccines* 90 (Cold Spring Harbor Laboratory Press); Carter, B. J. (1992) *Current Opinion in Biotechnology* 3:533–539; Muzyczka, N. (1992) *Current Topics in Microbiol. and Immunol.* 158:97–129; and Kotin, R. M. (1994) *Human Gene Therapy* 5:793–801.

Recombinant AAV (rAAV) virions are generally produced in a suitable host cell that has been transfected with two constructs including an AAV vector plasmid and a helper plasmid, whereby the host cell is thus capable of expressing the AAV proteins necessary for AAV replication and packaging (AAV helper functions). The host cell is then co-infected with an appropriate helper virus to provide necessary viral helper functions. AAV helper functions can be provided by transfecting the host cell with an AAV helper plasmid that includes the AAV rep and/or cap coding regions but which lacks the AAV ITRs. Accordingly, the helper plasmid can neither replicate nor package itself. A number of vectors that contain the rep coding region are known, including those vectors described in U.S. Pat. No. 5,139,941, having ATCC accession numbers 53222, 53223, 53224, 53225 and 53226. Similarly, methods of obtaining vectors containing the HHV-6 homologue of AAV rep are described in Thomson et al. (1994) *Virology* 204:304–311. A number of vectors containing the cap coding region have also been described, including those vectors described in U.S. Pat. No. 5,139,941. Packaging cell lines derived from human 293 cells that have been transfected with a vector having the AAV rep gene operably linked to a heterologous transcription promoter have been described in International Publication Nos. WO 95/13392, published 18 May 1995, and WO 95/13365, published 18 May 1995.

In rAAV virion production, AAV vector plasmids can be engineered to contain a functionally relevant nucleotide sequence (e.g., a selected gene, antisense nucleic acid molecule, ribozyme, or the like) of interest that is flanked by AAV ITRs which provide for AAV replication and packaging functions. Both AAV helper plasmids and the AAV vector plasmid bearing the nucleotide sequence are introduced into recipient cells by transient transfection. The transfected cells are then infected with adenovirus which transactivates the AAV promoters present on the helper plasmid that direct the transcription and translation of AAV rep and cap regions. rAAV virions harboring the nucleotide sequence of interest are formed and can be purified from the preparation.

A host cell that has been transfected with a helper plasmid encoding AAV helper functions comprises a packaging cell which, by virtue of the transfection, is capable of expressing AAV gene products to complement necessary functions deleted from a selected AAV vector plasmid. A number of attempts have been made to establish packaging cell systems. Particularly, Mendelson et al. (1988) *Virology* 166:154–165 reported a cell line capable of low level expression of one of the short forms of Rep using stable transfection of HeLa or 293 cells with plasmids containing the rep gene. Cell lines containing integrated AAV rep and cap genes expressed from the normal AAV promoters have also been described. Vincent et al. (1990) *Vaccines* 90, Cold Spring Harbor Laboratory Press, pp. 353–359.

Other approaches have attempted to establish packaging cell line systems containing AAV vectors, either stably integrated into the host cell genome, or maintained as an episomal plasmid. The cell lines are then transfected with trans complementing AAV functions such as with constructs containing the AAV rep, or rep and cap genes. See, e.g., U.S. Pat. No. 5,173,414 to Lebkowski, and International Publication Nos. WO 95/13365, published 18 May 1995 and WO 95/13392, published 18 May 1995.

However, a number of problems have been encountered in the aforementioned packaging cell systems which have greatly limited their utility. Particularly, such systems have not been able to generate significant levels of recombinant AAV virions. Not being bound by any particular theory, such problems may be due in part to several inhibitory effects attributed to expressed rep gene products in those cell systems. See, e.g., Labow et al. (1987) *Mol. Cell. Biol.* 7:1320–1325 and Tratschin et al. (1986) *Mol. Cell. Biol.* 6:2884–2894. Another problem has been the production of significant levels of contaminating wild-type AAV particles in such packaging cell systems due to recombination events between AAV vector and helper plasmid sequences. Senapathy et al. (1984) *J. Biol. Chem.* 259:4661–4666.

Accordingly, there remains a need to provide improved AAV helper function constructs that are capable of being expressed in a host cell at efficient levels. Further, there remains a need to provide AAV packaging cell systems capable of producing commercially significant levels of recombinant AAV particles without also generating significant levels of contaminating recombined wild-type AAV particles.

SUMMARY OF THE INVENTION

The present invention provides for novel nucleic acid molecules having nucleotide sequences that are substantially homologous to AAV p5 promoter regions and AAV coding regions (e.g., AAV rep and cap coding regions), wherein the p5 promoter region is situated in the nucleic acid molecule in a site other than its normal position relative to the AAV rep coding region in the wild-type AAV genome. The subject molecules, having a p5 promoter region which has been effectively moved from its normal upstream position (relative to the rep coding region in the wild-type (wt) AAV genome) exhibit several novel features. First, relocation of the p5 promoter region may result in an attenuation of the production of at least the long form Rep products when the rep coding region is expressed. Further, the cis acting functions necessary for expression from the AAV p19 and p40 promoters are present such that rep52/40 and cap appear to be normally expressed. Also, in particular molecules, the unwanted generation of contaminating wt AAV particles during rAAV production can be reduced or eliminated.

Also provided herein are nucleic acid molecules having AAV coding regions (e.g., AAV rep and cap coding regions) and a nucleotide sequence that comprises an AAV p5 promoter region, wherein the nucleotide sequence is arranged in the molecule such that the p5 promoter is situated in a site other than its normal upstream position relative to the AAV rep coding region in the wt AAV genome.

The above-described nucleic acid molecules can further include one, or a plurality of additional nucleotide sequences—wherein the single additional nucleotide sequence is arranged 5' to the AAV coding regions and the p5 promoter region, or the plurality of additional nucleotide sequences are arranged to flank the AAV coding regions and the p5 promoter region. These additional nucleotide sequences are substantially homologous to yeast FLP recombinase substrates (e.g., Flip Recombination Target (FRT) sites). Provision of 5' and 3' flanking FRT sites allows for the excision of the nucleic acid molecule from a vector construct by the action of the FLP recombinase enzyme.

The present invention also provides for AAV helper constructs that are capable of being expressed to provide AAV Rep and Cap polypeptides. Such helper constructs can be formed by operably linking the nucleic acid molecules of the invention to suitable control elements that are capable of directing the transcription and translation of the AAV coding regions contained in the constructs. The AAV helper constructs provided herein can comprise plasmids or any other suitable vector, and can further be constructed to include selectable genetic markers such as antibiotic resistance genes or the like. In one particular embodiment, the AAV helper construct comprises the plasmid pGN1909 (ATCC Accession Number 69871).

The invention further provides for AAV packaging cells that are capable of becoming AAV producing cells when an AAV vector is present therein and the packaging cell is capable of expressing viral helper functions. The subject AAV packaging cells are produced by introducing the AAV helper constructs of the present invention into a suitable host cell. More particularly, the helper constructs can be either transiently or stably transfected into suitable host cells using known techniques.

Also provided herein are AAV producer cells that are capable of producing rAAV virions when viral helper functions are expressed therein. The subject producer cells are formed by transfection of the AAV packaging cells of the present invention with a suitable AAV vector. In accordance with the invention, the AAV vector generally comprises a heterologous nucleotide sequence that is flanked by functional AAV ITRs. The production of rAAV virions that contain the heterologous nucleotide sequence (for subsequent transduction) can be accomplished by introducing viral helper functions into the producer cells to transactivate the AAV helper functions present in the AAV helper constructs.

The invention further provides methods of producing rAAV virions which include the steps of: introducing an AAV vector into a suitable host cell; introducing an AAV helper construct selected from those provided herein into the host cell to express essential AAV helper functions; expressing viral helper functions in the host cell; and culturing the cell to produce rAAV virions. The AAV vector and AAV helper constructs can be transfected into the host cell, either sequentially or simultaneously, using techniques known to those of skill in the art. The expression of viral helper functions can be provided by infecting the host cell with a suitable helper virus selected from the group of adenoviruses, herpesviruses and vaccinia viruses. The viral helper functions transactivate AAV promoters present in the AAV helper construct that direct the transcription and translation of AAV rep and cap regions. Thus, rAAV virions harboring a selected heterologous nucleotide sequence are formed and can be purified from the preparation using known methods.

These and other embodiments of the subject invention will readily occur to those of ordinary skill in the art in view of the disclosure herein.

BRIEF DESCRIPTION OF THE FIGURES

FIG. 3 shows the nucleotide sequences of a 76 bp FRT site [SEQ ID NO:3] and a 59 bp "minimum" FRT site [SEQ ID NO:2] that are useful in the construction of the AAV helper constructs of the present invention.

FIG. 4 depicts a polynucleotide sequence consisting of base pairs 145 through 494 [SEQ ID NO:4] of the wild-type AAV serotype 2 genome.

DETAILED DESCRIPTION OF THE INVENTION

Figure 1:
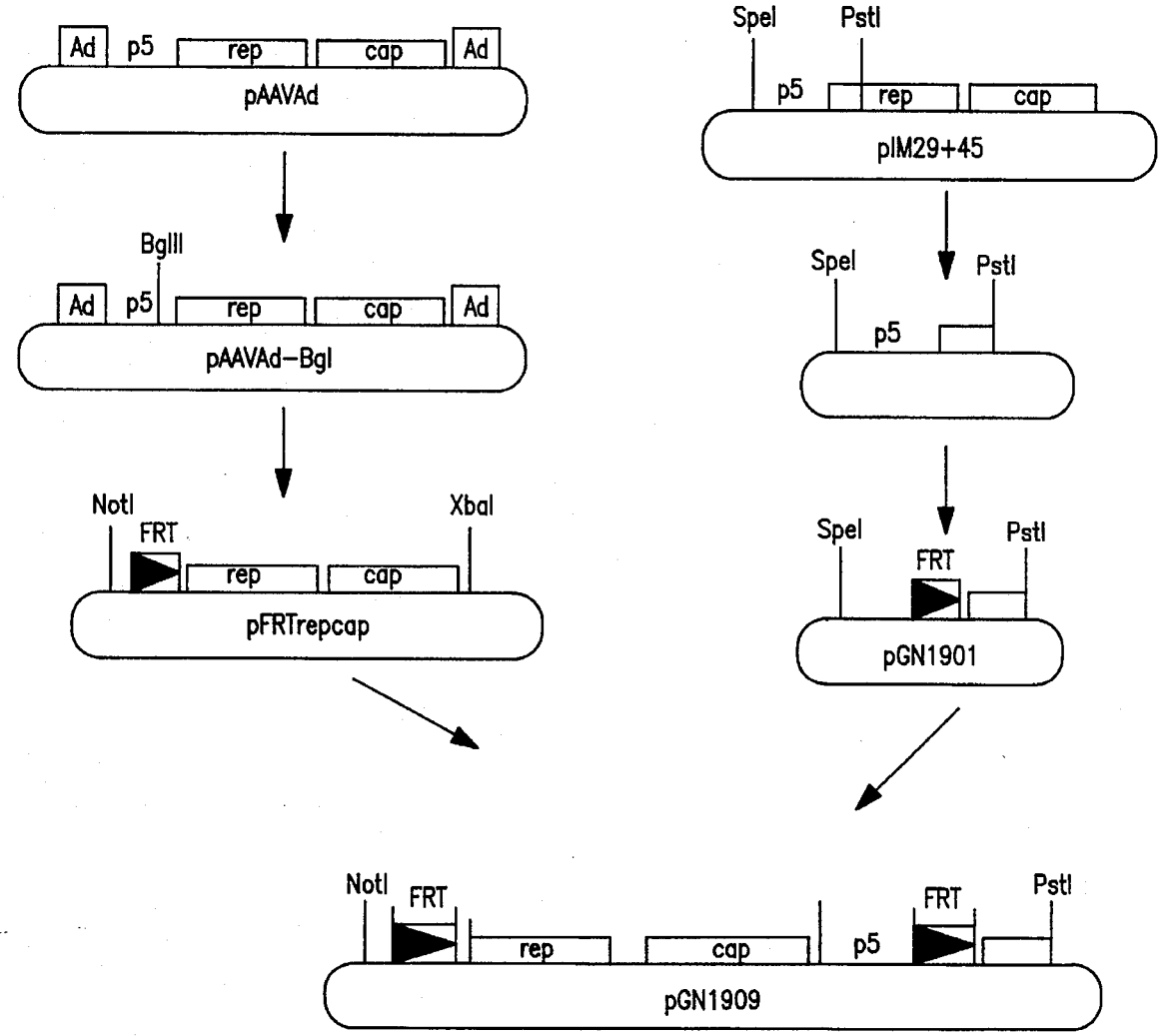
FIG. 1 depicts the construction of the pGN1909 plasmid construct.

The practice of the present invention will employ, unless otherwise indicated, conventional methods of virology, microbiology, molecular biology and recombinant DNA techniques within the skill of the art. Such techniques are explained fully in the literature. See, e.g., Sambrook, et al. *Molecular Cloning: A Laboratory Manual* (Current Edition); *DNA Cloning: A Practical Approach*, vol. I & II (D. Glover, ed.); *Oligonucleotide Synthesis* (N. Gait, ed., Current Edition); *Nucleic Acid Hybridization* (B. Hames & S. Higgins, eds., Current Edition); *Transcription and Translation* (B. Hames & S. Higgins, eds., Current Edition); *CRC Handbook of Parvoviruses*, vol. I & II (P. Tijessen, ed.); *Fundamental Virology*, 2nd Edition, vol. I & II (B. N. Fields and D. M. Knipe, eds.)

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

A. Definitions

In describing the present invention, the following terms will be employed, and are intended to be defined as indicated below.

"Gene transfer" or "gene delivery" refers to methods or systems for reliably inserting foreign DNA into host cells. Such methods can result in transient expression of non-integrated transferred DNA, extrachromosomal replication and expression of transferred replicons (e.g., episomes), or integration of transferred genetic material into the genomic DNA of host cells. Gene transfer provides a unique approach for the treatment of acquired and inherited diseases. A number of systems have been developed for gene transfer into mammalian cells. See, e.g., U.S. Pat. No. 5,399,346.

By "vector" is meant any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

By "adeno-associated virus inverted terminal repeats" or "AAV ITRs" is meant the art-recognized palindromic regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome.

The nucleotide sequences of AAV ITR regions are known. See, e.g., Kotin, R. M. (1994) *Human Gene Therapy* 5:793–801; Berns, K. I. "Parvoviridae and their Replication" in *Fundamental Virology*, 2nd Edition, (B. N. Fields and D. M. Knipe, eds.) for the AAV-2 sequence. As used herein, an "AAV ITR" need not have the wild-type nucleotide sequence depicted, but may be altered, e.g., by the insertion, deletion or substitution of nucleotides. Additionally, the AAV ITR may be derived from any of several AAV serotypes, including without limitation, AAV-1, AAV-2, AAV-3, AAV-4, AAV-5, AAVX7, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when the rep gene is present in the cell (either on the same or on a different vector).

By an "AAV vector" is meant a vector derived from an adeno-associated virus serotype, including without limitation, AAV-1, AAV-2, AAV-3, AAV-4, AAV-5, AAVX7, etc. AAV vectors can have one or more of the AAV wild-type genes deleted in whole or part, preferably the rep and/or cap genes, but retain functional flanking ITR sequences. Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging.

AAV vectors can be constructed using recombinant techniques that are known in the art to include one or more heterologous nucleotide sequences flanked on both ends (5' and 3') with functional AAV ITRs. In the practice of the invention, an AAV vector can include at least one AAV ITR and a suitable promoter sequence positioned upstream of the heterologous nucleotide sequence and at least one AAV ITR positioned downstream of the heterologous sequence. The 5' and 3' ITRs need not necessarily be identical or derived from the same AAV isolate, so long as they function as intended.

The selected heterologous nucleotide sequence included in the AAV vector can comprise any desired gene that encodes a protein that is defective or missing from a recipient cell genome or that encodes a non-native protein having a desired biological or therapeutic effect (e.g., an antiviral function), or the sequence can correspond to a molecule having an antisense or ribozyme function. Suitable genes include those used for the treatment of inflammatory diseases, autoimmune, chronic and infectious diseases, including such disorders as AIDS, cancer, neurological diseases, cardiovascular disease, hypercholestemia; various blood disorders including various anemias, thalasemias and hemophilia; genetic defects such as cystic fibrosis, Gaucher's Disease, adenosine deaminase (ADA) deficiency, emphysema, etc. A number of antisense oligonucleotides (e.g., short oligonucleotides complementary to sequences around the translational initiation site (AUG codon) of an mRNA) that are useful in antisense therapy for cancer and for viral diseases have been described in the art. See, e.g., Han et al. (1991) *Proc. Natl. Acad. Sci. USA* 88:4313–4317; Uhlmann et al. (1990) *Chem. Rev.* 90:543–584; Helene et al. (1990) *Biochim. Biophys. Acta.* 1049:99–125; Agarwal et al. (1988) *Proc. Natl. Acad. Sci. USA* 85:7079–7083; and Heikkila et al. (1987) *Nature* 328:445–449. For a discussion of suitable ribozymes, see, e.g., Cech et al. (1992) *J. Biol. Chem.* 267:17479–17482 and U.S. Pat. No. 5,225,347 to Goldberg et al.

AAV vectors can also include control sequences, such as promoter and polyadenylation sites, as well as selectable markers or reporter genes, enhancer sequences, and other control elements which allow for the induction of transcription. Such control elements are described more fully below. Such AAV vectors can be constructed using techniques well known in the art. See, e.g., U.S. Pat. No. 5,173,414; International Publication Numbers WO 92/01070 (published 23 Jan. 1992) and WO 93/03769 (published 4 Mar. 1993);

Lebkowski et al. (1988) *Molec. Cell. Biol.* 8:3988–3996; Vincent et al. (1990) *Vaccines* 90 (Cold Spring Harbor Laboratory Press); Carter, B. J. (1992) *Current Opinion in Biotechnology* 3:533–539; Muzyczka, N. (1992) *Current Topics in Microbiol. and Immunol.* 158:97–129; Kotin, R. M. (1994) *Human Gene Therapy* 5:793–801; Shelling and Smith (1994) *Gene Therapy* 1:165–169; and Zhou et al. (1994) *J. Exp. Med.* 179:1867–1875.

"AAV helper functions" refer to AAV-derived coding sequences which can be expressed to provide AAV gene products that, in turn, can function in trans for productive AAV replication. Thus, AAV helper functions include one, or both of the major AAV open reading frames (ORFs)—rep and cap. The Rep expression products have been shown to possess many functions, including recognition, binding and nicking of the AAV origin of DNA replication; DNA helicase activity; and modulation of transcription from AAV (or other heterologous) promoters. The Cap expression products supply necessary packaging functions. AAV helper functions are used herein to complement AAV functions in trans that are missing from AAV vectors.

The term "viral helper functions" refers to the provision of factors that are necessary during various aspects of the AAV life cycle. AAV requires such helper functions from an unrelated helper virus (e.g., an adenovirus, a herpesvirus or a vaccinia virus), in order for a productive AAV infection to occur. Particularly, it has been demonstrated that adenovirus supplies factors required for AAV promoter expression, AAV messenger RNA stability and AAV translation. See, e.g., Muzyczka, N. (1992) *Curr. Topics. Microbiol. and Immun.* 158:97–129. In the absence of such functions, AAV establishes a latent state by insertion of its genome into a host cell chromosome. Production of viral helper functions rescues the integrated copy which can then replicate to produce infectious viral progeny. Viral helper functions can be provided by infection of a cell with a suitable helper virus.

The term "AAV helper construct" refers generally to a nucleic acid molecule that includes nucleotide sequences providing AAV functions deleted from an AAV vector which is to be used to produce a transducing vector for delivery of a nucleotide sequence of interest. AAV helper constructs are commonly used to provide transient expression of AAV rep and/or cap genes to complement missing AAV functions that are necessary for lytic AAV replication; however, helper constructs lack AAV ITRs and can neither replicate nor package themselves. AAV helper constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al. (1989) *J. Virol.* 63:3822–3828; and McCarty et al. (1991) *J. Virol.* 65:2936–2945. A number of other vectors have been described which encode Rep and/or Cap expression products. See, e.g., U.S. Pat. No. 5,139,941.

By "recombinant virus" is meant a virus that has been genetically altered, e.g., by the addition or insertion of a heterologous nucleic acid construct into the particle.

By "AAV virion" is meant a complete virus particle, such as a wild-type (wt) AAV virus particle (comprising a linear, single-stranded AAV nucleic acid genome associated with an AAV capsid protein coat), or a recombinant AAV virus particle as described below. In this regard, single-stranded AAV nucleic acid molecules of either complementary sense, e.g., "sense" or "antisense" strands, can be packaged into any one AAV virion and both strands are equally infectious.

A "recombinant AAV virion," or "rAAV virion" is defined herein as an infectious, replication-defective virus composed of an AAV protein shell, encapsidating a heterologous nucleotide sequence of interest which is flanked on both sides by AAV ITRs.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. Certain consensus sequences within the promoter region are deemed to be particularly important in the binding of RNA polymerase, and are generally referred to as CAT and TATA boxes. Promoter regions extend from about 40 nucleotides to about 5 nucleotides upstream from the start of the gene-coding region, the CAT and TATA boxes being located within the promoter region as short stretches of nucleotide sequences. The TATA box includes the binding site of transcription factors, but not of the RNA polymerase enzyme.

An "AAV p5 promoter region" encompasses both promoter sequences with identity to a p5 promoter region isolated from an AAV serotype, including without limitation, AAV-1, AAV-2, AAV-3, AAV-4, AAV-5, AAVX7, etc., as well as those which are substantially homologous and functionally equivalent thereto (as defined below). The AAV p5 promoter directs the expression of the long forms of Rep, and has been described and characterized. See, e.g., Lusby et al. (1982) *J. Virol.* 41:518–526; Laughlin et al. (1979) *Proc. Natl. Acad. Sci. USA* 76:5567–5571; Green et al. (1980a) *J. Virol.* 36:79–92; Green et al. (1980b) *Cell* 1:231–242. For purposes of defining the present invention, in the wt AAV genome, the AAV p5 promoter region is "in its natural position" when it is bound at the 5'-terminus of the transcriptional start site of the rep coding sequence and the rep transcriptional start site is approximately 25 bps downstream (3'-direction) from the p5 TATA box, such that the rep ATG is approximately 60 bps downstream (3'-direction) from the p5 TATA box. The wt AAV p5 promoter extends upstream (5'-direction) to include the minimum number of bases or elements necessary to initiate transcription of the long forms of Rep at levels detectable above background.

An AAV p5 promoter region is situated "other than in its natural position" when the AAV p5 promoter has been moved from its natural position relative to the rep coding sequence in the particular nucleic acid molecule being described. For example, an AAV p5 promoter region "is situated other than in its natural position" when that region is situated in a nucleic acid molecule such that the AAV p5 promoter TATA box is not 25 bps upstream (5'-direction) of the rep transcriptional start site in that same molecule.

By "AAV rep coding region" is meant the art-recognized region of the AAV genome which encodes the replication proteins of the virus which are collectively required for replicating the viral genome, or functional homologues thereof such as the human herpesvirus 6 (HHV-6) rep gene which is also known to mediate AAV-2 DNA replication (Thomson et al. (1994) *Virology* 204:304–311). Thus, the rep coding region includes at least the genes encoding for AAV Rep 78, Rep 68, Rep 52 and Rep 40, or functional homologues thereof. As used herein, the rep coding region does not include the AAV p5 promoter region. For a further description of the AAV rep coding region, see, e.g., Muzyczka, N. (1992) *Current Topics in Microbiol. and Immunol.* 158:97–129; and Kotin, R. M. (1994) *Human Gene Therapy* 5:793–801. The rep coding region can be derived from any serotype, such as those AAV serotypes described above. The region need not include all of the wild-type genes but may be altered, e.g., by the insertion, deletion or substitution of nucleotides, so long as the rep genes present provide for sufficient replication functions when present in a host cell along with an AAV vector.

The term "short forms of Rep" refers to the Rep 52 and Rep 40 gene products of the AAV rep coding region, including functional homologues thereof. The short forms of Rep are expressed under the direction of the AAV p19 promoter which has been described and characterized. See e.g., Lusby et al., Laughlin et al., Green et al. (1980a) and Green et al. (1980b), supra.

The term "long forms of Rep" refers to the Rep 78 and Rep 68 gene products of the AAV rep coding region, including functional homologues thereof. The long forms of Rep are normally expressed under the direction of the AAV p5 promoter which has been described and characterized. See, Lusby et al., Laughlin et al., Green et al. (1980a) and Green et al. (1980b), supra.

By "AAV cap coding region" is meant the art-recognized region of the AAV genome which encodes the coat proteins of the virus which are collectively required for packaging the viral genome. Thus, the cap coding region includes at least the genes encoding for the coat proteins VP1, VP2 and VP3. For a further description of the cap coding region, see, e.g., Muzyczka, N. (1992) *Current Topics in Microbiol. and Immunol.* 158:97–129; and Kotin, R. M. (1994) *Human Gene Therapy* 5:793–801. The AAV cap coding region, as used herein, can be derived from any AAV serotype, as described above. The region need not include all of the wild-type cap genes but may be altered, e.g., by the insertion, deletion or substitution of nucleotides, so long as the genes provide for sufficient packaging functions when present in a host cell along with an AAV vector.

By an "AAV coding region" is meant a nucleic acid molecule which includes the two major AAV open reading frames corresponding to the AAV rep and cap coding regions (e.g., a nucleic acid molecule comprising a nucleotide sequence substantially homologous to base pairs 310 through 4,440 of the wild-type AAV genome). See, e.g., Srivastava et al. (1983) *J. Virol.* 45:555–564; Hermonat et al. (1984) *J. Virol.* 51:329–339; and Tratschin et al. (1984) *J. Virol.* 51:611–619. Thus, for purposes of the present invention, an "AAV coding region" does not include those sequences corresponding to the AAV p5 promoter region, and does not include the AAV ITRs.

A "Flip Recombination Target site" (FRT) refers to a nucleotide sequence that serves as a substrate in the site-specific yeast flip recombinase system. The FRT recombination region has been mapped to an approximately 65-base pair (bp) segment within the 599-bp long inverted repeats of the 2-µm circle (a commonly occurring plasmid in *Saccharomyces cerevisiae*). The enzyme responsible for recombination (FLP) is encoded by the 2-µm circle, and has been expressed at high levels in human cells. FLP catalyzes recombination within the inverted repeats of the molecule to cause intramolecular inversion. FLP can also promote efficient recombination between plasmids containing the 2-µm circle repeat with very high efficiency and specificity. See, e.g., Jayaram (1985) *Proc. Natl. Acad. Sci. USA* 82:5875–5879; and O'Gorman (1991) *Science* 251:1351–1355. A "minimum FRT site" (e.g., a minimal FLP substrate) has been described in the art and is defined herein as a 13-bp dyad symmetry plus an 8-bp core located within the 65-bp FRT region. Jayaram et al., supra. Both FRT sites and FLP expression plasmids are commercially available from Stratagene (San, Diego, Calif.).

"Transfection" refers to the uptake of foreign DNA by a cell, and a cell has been "transfected" when exogenous DNA has been introduced inside the cell membrane. In this manner, the exogenous DNA may or may not become integrated (covalently linked) to chromosomal DNA making up the genome of the cell. A number of transfection techniques are known in the art. See, e.g., Graham et al. (1973) *Virology,* 52:456, Sambrook et al. (1989) *Molecular Cloning, a laboratory manual,* Cold Spring Harbor Laboratories, New York, Davis et al. (1986) *Basic Methods in Molecular Biology,* Elsevier, and Chu et al. (1981) *Gene* 13:197. Any of these techniques can be used to introduce one or more exogenous DNA moieties, such as AAV helper constructs, AAV vector plasmids, and other vector constructs, into suitable host cells. Generally, the exogenous DNA must traverse the recipient cell plasma membrane in order to be exposed to the cell's transcription and replication machinery. The resulting cell can either be transiently transfected with the exogenous nucleic acid molecule, or stably transfected—wherein the nucleic acid molecule is covalently linked with the host cell genome or maintained and replicated as an episomal unit which can be passed on to progeny cells (e.g., capable of extra-chromosomal replication at a sufficient rate). Such transfection methods have been described in the art, including calcium phosphate co-precipitation (Graham et al. (1973) *Virol.* 52:456–467), direct micro-injection into cultured cells (Capecchi, M. R. (1980) *Cell* 22:479–488), electroporation (Shigekawa et al. (1988) *BioTechniques* 6:742–751), liposome mediated gene transfer (Mannino et al. (1988) *BioTechniques* 6:682–690), lipid-mediated transfection (Felgner et al. (1987) *Proc. Natl. Acad. Sci. USA* 84:7413–7417), and nucleic acid delivery using high-velocity microprojectiles (Klein et al. (1987) *Nature* 327:70–73).

"Transient transfection" refers to cases where exogenous DNA does not integrate into the genome of a transfected cell, e.g., where episomal DNA is transcribed into mRNA and translated into protein.

A cell has been "stably transfected" with a nucleic acid construct comprising AAV coding regions when the nucleic acid construct has been introduced inside the cell membrane and the AAV coding regions are capable of being inherited by daughter cells.

The term "host cell" denotes, for example, microorganisms, yeast cells, insect cells, and mammalian cells, that can be, or have been, used as recipients of an AAV helper construct, an AAV vector plasmid, or other transfer DNA, and include the progeny of the original cell which has been transfected. Thus, a "host cell" as used herein generally refers to a cell which has been transfected with an exogenous DNA sequence using methods as described above. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

A "packaging cell" refers to a host cell which, by way of stable or transient transfection with heterologous nucleotide sequences, harbors a nucleic acid molecule comprising an AAV helper construct, wherein the construct is capable of providing transient expression of AAV helper functions that can be provided in trans for productive AAV replication. Expression of the AAV helper functions can be either constitutive, or inducible, such as when the helper functions are under the control of an inducible promoter.

A "producer cell" refers to a packaging cell that has been stably or transiently transfected with an AAV vector—either before, subsequent to, or at the same time as transfection of the cell with the AAV helper functions. In this manner, a producer cell contains AAV sequences that are provided in cis for replication and packaging (e.g., functional ITR sequences), and AAV sequences encoding helper functions missing from the AAV vector and provided in trans for replication and packaging. In the presence of requisite viral helper functions, the producer cell is thus capable of encoding AAV polypeptides that are required for packaging transfected viral DNA (e.g., AAV viral vectors containing a recombinant nucleotide sequence of interest) into infectious viral particles for subsequent gene delivery.

Viral helper functions, as defined above, can be introduced into a producer cell by infection or superinfection thereof with one or more helper virus moiety such as an adenovirus, herpesvirus or vaccinia virus.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct is a segment of nucleic acid within or attached to another nucleic acid molecule that is not found in association with the other molecule in nature. For example, a heterologous region of a construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a host cell transformed with a construct which is not normally present in the cell would be considered heterologous for purposes of this invention. Allelic variation or naturally occurring mutational events do not give rise to heterologous DNA, as used herein.

A "coding sequence" or a sequence which "encodes" a particular polypeptide, is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from procaryotic or eukaryotic mRNA, genomic DNA sequences from procaryotic or eukaryotic DNA, and even synthetic DNA sequences. A transcription termination sequence will usually be located 3' to the coding sequence.

The term DNA "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected gene is capable of being replicated, transcribed and translated in an appropriate recipient cell.

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

By "isolated" when referring to a nucleotide sequence, is meant that the indicated molecule is present in the substantial absence of other biological macromolecules of the same type. Thus, an "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

For the purpose of describing the relative position of nucleotide sequences in a particular nucleic acid molecule throughout the instant application, such as when a particular nucleotide sequence is described as being situated "upstream," "downstream," "3'," or "5'" relative to another sequence, it is to be understood that it is the position of the sequences in the "sense" or "coding" strand of a DNA molecule that is being referred to as is conventional in the art.

"Homology" refers to the percent of identity between two polynucleotide or two polypeptide moieties. The correspondence between the sequence from one moiety to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single-stranded-specific nuclease(s), and size determination of the digested fragments. Two DNA, or two polypeptide sequences are "substantially homologous" to each other when at least about 80%, preferably at least about 90%, and most preferably at least about 95% of the nucleotides or amino acids match over a defined length of the molecules, as determined using the methods above.

A "functional homologue," or a "functional equivalent" of a given polypeptide includes molecules derived from the native polypeptide sequence, as well as recombinantly produced or chemically synthesized polypeptides which function in a manner similar to the reference molecule to achieve a desired result. Thus, a functional homologue of AAV Rep 52 or Rep 40 encompasses derivatives and analogues of those polypeptides—including any single or multiple amino acid additions, substitutions and/or deletions occurring internally or at the amino or carboxy termini thereof, so long as replication activity remains.

A "functional homologue," or a "functional equivalent" of a given AAV promoter region includes promoters derived from an AAV serotype, as well as recombinantly produced or chemically synthesized polynucleotides which function in a manner similar to the reference promoter region to achieve a desired result. Thus, a functional homologue of an AAV p5 promoter region encompasses derivatives and analogues of such control sequences—including any single or multiple nucleotide base additions, substitutions and/or deletions occurring within the promoter region, so long as the promoter homologue retains the minimum number of bases or elements sufficient to initiate transcription of the long forms of Rep at levels detectable above background.

B. General Methods

It is a primary object of the invention to provide improved AAV helper systems useful in the production of recombinant AAV (rAAV) virions that can subsequently be used in gene transfer methods. Particularly, it is an object of the invention to develop AAV helper constructs that can be introduced into suitable packaging cells to provide for enhanced production of commercially useful levels of recombinant AAV virions.

In one particular embodiment, a nucleic acid molecule is provided having an AAV rep and cap coding region and an AAV p5 promoter region that is situated in the subject molecule at a site that is other than its normal upstream position relative to the AAV rep coding region in a wild-type (wt) AAV genome. The rep and cap coding regions can be arranged in the molecule as two contiguous main open reading frames, respectively arranged in the order given in the 5' to 3' direction such as the normal arrangement of those coding regions in the wt AAV genome. See, e.g., Berns and Bohenzky (1987) *Advances in Virus Research* (Academic Press, Inc.) 32:243–307; Tratschin et al. (1984) *J. Virol.* 51:611–619; and Srivastava et al. (1983) *J. Virol.* 45:555–564.

Alternatively, the rep and cap coding regions can be arranged in the nucleic acid molecule as two non-contiguous regions separated by intervening nucleotides and arranged in any order—so long as the rep coding region includes at least one promoter capable of directing the expression of rep52/40 (such as a nucleotide sequence that is substantially homologous to an AAV p19 promoter region), and the cap coding region includes at least one promoter capable of directing the expression of the Cap expression products (such as a nucleotide sequence that is substantially homologous to an AAV p40 promoter region).

The instant molecules can be constructed by linking nucleotide sequences corresponding to AAV rep and cap coding regions (Srivastava et al., supra.) with a nucleotide sequence that is substantially homologous to an AAV p5 promoter region, or that corresponds to bps 145–309 of the wt AAV genome (Srivasta et al., supra)—wherein the p5 promoter region is arranged in the molecule in any position other than its normal position relative to the rep coding region. In one particular molecule, the nucleotide sequence that comprises the AAV p5 promoter region is substantially homologous to bps 145–494 of the wt AAV genome (Srivasta et al., supra). In another molecule, the nucleotide sequence that is homologous to the AAV p5 promoter region is positioned downstream from both the rep and cap coding regions, substantially adjacent to the 3' terminus of the cap coding region. By substantially adjacent to the 3' terminus is meant that the subject nucleotide sequence is within about 0 to 500 nucleotides, more preferably within about 0 to 200 nucleotides, and most preferably within about 0 to 50 nucleotides of the 3' terminus of the cap coding region.

In yet another embodiment, the AAV p5 promoter region is positioned downstream from both the rep and cap coding regions and separated therefrom by an intervening nucleotide sequence (X) having a minimum length (l), whereby the resultant AAV rep-cap-X-p5 fragment is sized such that recombination events (during recombinant AAV virion production) between said fragment and an AAV vector (resulting in an acquisition of ITRs) will yield a recombined molecule that is too large to package as an AAV virion. It is generally recognized that an approximately 5100 bp fragment represents the upper limit of genetic material which can be packaged in such particles (see, e.g., U.S. Pat. No. 5,173,414 to Lebkowski et al.). In this way, the potential production of contaminating wt AAV particles is reduced or eliminated.

The above-described nucleic acid molecules can be isolated and cloned into a suitable vector such as a plasmid or virus particle to provide an AAV helper construct, wherein the vector can further include suitable control elements for replication and expression of the AAV coding sequences and facilitates the transfer of the nucleic acid molecule between cells.

In additional embodiments of the invention, the above-described nucleic acid molecules can include one or more nucleotide sequences that are substantially homologous to yeast FLP recombinase substrates (e.g. Flip Recombination Target (FRT) sites). Jayaram (1985) *Proc. Natl. Acad. Sci. USA* 82:5875–5879; and O'Gorman (1991) *Science* 251:1351–1355. Thus, the above-described nucleic acid molecules can include a second nucleotide sequence that is homologous to an FRT site (or at least a minimum FRT site), wherein the second nucleotide sequence is arranged in the molecule such that the FRT site is situated upstream of the AAV coding regions and the AAV p5 promoter region. In preferred embodiments, molecules are provided which comprise, in the 5' to 3' direction, an FRT site (Jayaram, and O'Gorman, supra), an AAV rep coding region, an AAV cap coding region, and an AAV p5 promoter region. In yet a further embodiment, a molecule is provided wherein the nucleotide sequence that contains the AAV p5 promoter region is substantially homologous to bps 145–494 of the wt AAV genome (Srivasta et al., supra). This first nucleotide sequence also has an inserted polynucleotide that comprises an FRT site. More particularly, a polynucleotide insert (comprising an FRT site) has been placed between bps 310 and 311 of the first sequence so that the inserted FRT site is situated immediately adjacent the 3' teminus of the AAV p5 promoter region (which extends from bps 145–310). The resultant construct is then positioned in the nucleic acid molecule to situate the AAV p5 promoter region in any position other than its normal position relative to the rep coding region, as has been described above. All of the aforementioned molecules can be constructed using recombinant techniques known in the art.

In related embodiments, the above-described nucleic acid molecules are constructed so as to include a plurality of polynucleotides that are homologous to an FRT site. More particularly, two FRT sites can be arranged in the molecules so that they provide 5' and 3' flanking regions bordering the AAV coding regions and AAV p5 promoter region. In this manner, the nucleic acid molecule comprises a cassette (having an AAV rep coding region, an AAV cap coding region and an AAV p5 promoter region) that is flanked by FRT sites. In preferred embodiments, the nucleic acid molecules are arranged such that they comprise, in the order given in the 5' to 3' direction, an FRT site, AAV rep, AAV cap, an AAV p5 promoter region, and an FRT site. The above molecules can be assembled, isolated and cloned into a suitable vector using known techniques. The FRT-rep-cap-p5-FRT cassette can be readily inserted into, or excised from a vector by the action of the yeast FLP recombinase enzyme if so desired.

In yet a further related embodiment, a molecule is provided having AAV rep and cap coding regions, a nucleotide sequence containing an AAV p5 promoter region, and a plurality of FRT sites. In this particular molecule, the nucleotide sequence that contains the AAV p5 promoter region is substantially homologous to bps 145–494 of the wt AAV genome (Srivasta et al., supra). Within this first nucleotide sequence, there has been inserted a polynucleotide that comprises an FRT site. More particularly, a polynucleotide insert (comprising an FRT site) has been placed between bps 310 and 311 of the first sequence so that the inserted FRT site is situated immediately adjacent the 3' terminus of the AAV p5 promoter region (which extends from bps 145–310). The nucleic acid molecule is then arranged such that it comprises, in the order given in the 5' to 3' direction, an FRT site, AAV rep, AAV cap, and a nucleotide sequence comprising an AAV p5 promoter region and having an FRT site situated immediately 3' of the AAV p5 promoter region.

Furthermore, vectors containing the above-described nucleic acid molecules are readily introduced into a suitable host and expressed therein to complement missing AAV functions in AAV vectors that lack functioning rep and/or cap coding regions. The rep and cap regions in an AAV vector can be disabled by deletions of genetic material, insertions of genetic material that cause reading frame errors and point mutations that disrupt the replication and encapsidation functions supplied by those genes. An AAV vector system can be screened for a functioning rep coding region by transfecting the vector into a suitable host, such as an adenovirus-infected cell, and assaying cell extracts, e.g., 48 hours later, for the presence of replicating vector genomes. If the rep coding region is functional, replicating DNA can be revealed by Southern blot analysis using techniques known in the art. AAV vector systems can be screened for a functioning cap coding region by assaying for AAV particle production using Western blot techniques that are known in the art (Samulski et al. (1989) *J. Virol.* 63:3822–3828).

The nucleic acid molecules of the present invention can be constructed using conventional recombinant techniques. In this regard, nucleic acid molecules containing AAV rep and cap coding regions with a displaced AAV p5 promoter region can be readily constructed by inserting a nucleotide sequence that includes an AAV p5 promoter region into a construct having an AAV coding region (containing rep and cap coding regions) by ligating a restriction fragment containing the subject promoter region into a suitable site relative to the AAV rep coding region. The newly formed nucleic acid molecule can then be excised from the construct using restriction enzymes if so desired. These and other molecules of the invention can thus be provided herein using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al. (1988) *Molec. Cell. Biol.* 8:3988–3996; Vincent et al. (1990) *Vaccines 90* (Cold Spring Harbor Laboratory Press); Carter, B. J. (1992) *Current Opinion in Biotechnology* 3:533–539; Muzyczka, N. (1992) *Current Topics in Microbiol. and Immunol.* 158:97–129; Kotin, R. M. (1994) *Human Gene Therapy* 5:793–801; Shelling and Smith (1994) *Gene Therapy* 1:165–169; and Zhou et al. (1994) *J. Exp. Med.* 179:1867–1875.

More particularly, selected AAV coding regions comprising the rep and cap genes, and selected nucleotide sequences such as those containing an AAV p5 promoter region, can be excised from the viral genome or from an AAV vector containing the same and linked such that the p5 promoter region is 3' of the rep and/or cap coding regions, using standard ligation techniques such as those described in Sambrook et al., supra. The molecules can be further constructed to have flanking FRT sequences arranged at their 5', or 5' and 3' ends. Ligations can be accomplished in 20 mM Tris-Cl pH 7.5, 10 mM MgCl$_2$, 10 mM DTT, 33 ug/ml BSA, 10 mM–50 mM NaCl, and either 40 uM ATP, 0.01–0.02 (Weiss) units T4 DNA ligase at 0° C. (for "sticky end" ligation) or 1 mM ATP, 0.3–0.6 (weiss) units T4 DNA ligase at 14° C. (for "blunt end" ligation). Intermolecular "sticky end" ligations are usually performed at 30–100 µg/ml total DNA concentrations (5–100 nM total end concentration).

In the alternative, the nucleic acid molecules of the invention can be synthetically derived, using a combination of solid phase direct oligonucleotide synthesis chemistry and enzymatic ligation methods which are conventional in the art. Synthetic sequences may be constructed having features such as restriction enzyme sites and can be prepared in commercially available oligonucleotide synthesis devices such as those devices available from Applied Biosystems, Inc. (Foster City, Calif.) using the phospharamidite method. See, e.g., Beaucage et al. (1981) *Tetrahedron Lett.* 22:1859–1862. The nucleotide sequences of the AAV rep and cap coding sequences, the AAV p5, p19 and p40 promoter regions, and FRT sites are known and have been previously described, (see, e.g., Srivastava et al. (1983) *J. Virol.* 45:555–564; Kotin, R. M. (1994) *Human Gene Therapy* 5:793–801; Berns, K. I. "Parvoviridae and their Replication" in *Fundamental Virology*, 2nd Edition, (B. N. Fields and D. M. Knipe, eds.) for AAV sequences; and, see, e.g., Jayaram et al. (1985) *Proc. Natl. Acad. Sci. USA* 82:5875–5879 and O'Gorman (1991) *Science* 251:1351–1355 for FRT sequences). Preferred codons for expression of the synthetic molecule in mammalian cells can also be synthesized. Complete nucleic acid molecules are then assembled from overlapping oligonucleotides prepared by the above methods. See, e.g., Edge, *Nature* (1981) 292:756; Nambair et al. *Science* (1984) 223:1299; Jay et al. *J. Biol. Chem.* (1984) 259:6311.

It is a further object of the invention to provide AAV helper constructs that generally comprise replicons including the nucleic acid molecules of the present invention. The constructs are thus capable of encoding AAV helper functions. A replicon is defined herein as any length of DNA that serves as a unit of replication during DNA synthesis. In one embodiment, an AAV helper construct is provided in the form of an episome that is capable of autonomous replication independently of a host genome, and which may further be capable of integration into a host chromosome. In one particularly preferred embodiment, the construct is a plasmid. In various other embodiments, the AAV helper functions (e.g., the rep and cap coding regions) are operably linked to control sequences that direct the transcription and translation thereof.

In one particular aspect of the invention, AAV helper constructs are assembled so as to provide expression cassettes that can be maintained as an extrachromosomal replicon (e.g., an episome or plasmid) that is capable of stable maintenance in a host cell. The construct will have an appropriate replication system allowing it to be substantially stably maintained in a replicating host.

AAV helper constructs which include the AAV rep and cap coding regions with an AAV p5 promoter region— arranged in the subject construct to be situated in a site other than its normal position relative to the rep coding region in the wt AAV genome—control sequences and optional amplification sequences, as described above, can also include selectable markers. Suitable markers include genes which confer antibiotic resistance or sensitivity, or impart color, or change the antigenic characteristics when cells which have been transfected with the nucleic acid constructs are grown in an appropriate selective medium. Particular selectable marker genes useful in the practice of the invention include the hygromycin B resistance gene (encoding Aminoglycoside phosphotranferase (APH)) that allows selection in mammalian cells by conferring resistance to G418 (available from Sigma, St. Louis, Mo.). Other suitable markers are known to those of skill in the art.

It is yet a further object of the invention to provide AAV packaging cells that are capable of producing rAAV virions when an AAV vector is present in the cell and the packaging cell is capable of expressing viral helper functions. In one particular embodiment, AAV packaging cells can be derived from mammalian cells which are able to sustain infection by a helper virus (for the provision of viral helper functions). In this regard, almost any mammalian cell can sustain AAV and produce AAV virions so long as a helper virus is present which is compatible with the cell. Therefore, packaging cells used to produce rAAV virions will be a matter of choice, largely dictated by convenience, such as availability, growth characteristics, or the like. Suitable packaging cells include, without limitation, cells derived from human and nonhuman primate species, rodent, bovine, ovine, porcine, equine, feline and canine cells, among others. However, due to convenience, human cell lines are preferred such as human 293, HeLa, KB and JW-2 cells. These cells are readily available through the American Type Culture Collection (ATCC) (e.g., human 293 cells are available under accession number ATCC CRL1573).

In one particular embodiment, an AAV packaging cell is formed from a suitable host cell (e.g., a human 293 cell) by transfecting the cell with an AAV helper construct capable of expressing AAV helper functions. The subject AAV helper construct comprises a nucleic acid molecule having AAV rep and cap coding regions and a nucleotide sequence comprising an AAV p5 promoter region, wherein the nucleotide sequences are arranged in the molecule so as to situate the p5 promoter region in a site that is other than its normal position relative the rep coding region in the wt AAV genome as has been described above. The helper construct is capable of being efficiently transcribed and translated in the host cell to complement missing AAV functions in an associated AAV vector.

In another particular embodiment, an AAV packaging cell is formed from a suitable host cell (e.g., a human 293 cell) by transfection with an AAV helper construct capable of expressing AAV Rep and Cap polypeptides. The transfected AAV helper construct comprises a nucleic acid molecule having an AAV coding region and a nucleotide sequence comprising an AAV p5 promoter region, said AAV coding region and said p5 promoter region respectively arranged 5' to 3' in the molecule and separated from each other by an intervening nucleotide sequence. The subject construct is capable of being efficiently transcribed and translated in the host cell to complement missing AAV functions in an associated AAV vector. Further, the intervening nucleotide sequence can be selected to have a sufficient length that renders the resultant AAV rep-cap . . . p5 fragment too large to package as an AAV virion particle in the event of recombination during rAAV virion production. In this manner, production of significant levels of contaminating wt AAV particles in the packaging cell system is avoided. In a related embodiment, the AAV helper construct comprises a plasmid.

Each of the AAV helper constructs of the invention can be stably maintained in the packaging cell as an episomal element or can be integrated into the packaging cell genome, thus creating a packaging cell line which can be maintained indefinitely. Alternatively, the AAV helper constructs can be transfected into the packaging cell either just prior or subsequent to, or concomitant with, introduction of suitable viral helper functions.

It is also an object of the present invention to provide AAV producer cells that are capable of producing rAAV virions when viral helper functions are expressed therein. In one particular embodiment, producer cells are formed by either transiently or stably transfecting one of the aforementioned AAV packaging cells with an AAV vector (such as a plasmid) harboring a heterologous nucleotide sequence that is interposed between functional AAV ITRs.

It is yet an even further object of the invention to provide methods for the production of rAAV virions, wherein the methods generally involve the steps of (1) introducing an AAV vector harboring a heterologous nucleotide sequence to be transduced that is interposed between functional AAV ITRs into a host cell; (2) introducing an AAV helper construct that has been assembled as described above into the host cell, wherein the construct is capable of expressing AAV helper functions missing from the AAV vector; (3) expressing viral helper functions in the host cell; and (4) culturing the cell to produce rAAV virions.

In one embodiment, a method of producing rAAV virions is provided wherein an AAV packaging cell that has been constructed as described above is transfected with an AAV vector containing a heterologous nucleotide sequence of interest that is interposed between AAV ITRs. The AAV packaging cell can be either transiently or stably transfected with the subject AAV vector (to provide a producer cell as has been described above).

In one preferred embodiment, the AAV packaging cell used in the above method is produced by transfecting a suitable host cell with an AAV helper construct capable of being expressed to provide AAV Rep and Cap polypeptides. The subject AAV helper construct comprises a nucleic acid molecule having AAV rep and cap coding regions and a nucleotide sequence comprising an AAV p5 promoter region, wherein the elements of the molecule are arranged such that the sequence comprising the p5 promoter region is relocated downstream relative to the AAV rep and cap coding regions. The AAV helper construct can be co-transfected into the host cell with an appropriate AAV vector using methods known to those skilled in the art. In further related embodiments, the AAV helper construct can include one or more flanking FRT sites as described supra.

In another preferred embodiment, an AAV packaging cell is produced by transfecting a suitable host cell with an AAV helper construct designed to reduce or eliminate the production of significant levels of wild-type AAV during rAAV vector production. The helper construct includes a nucleic acid molecule having AAV rep and cap coding regions, an intervening nucleotide sequence, and a nucleotide sequence comprising an AAV p5 promoter region. The elements of the molecule are arranged such that the AAV p5 promoter region is positioned downstream from both the rep and cap coding regions and separated therefrom by the intervening nucleotide sequence (X). The nucleotide sequence (X) is selected to have a minimum length such that the resultant AAV rep-cap-X-p5 fragment will have an overall size that is effective to ensure that recombination events (during recombinant AAV virion production) between said fragment and an AAV vector (resulting in an acquisition of ITRs) will yield a recombined molecule that is too large to package as an AAV virion. In this manner, the potential production of wt AAV particles is reduced or eliminated.

In the practice of the invention, enhanced titers of rAAV virions can be obtained using methods which employ the above-described packaging cells. Not being bound by any particular theory, enhanced virion production in such cells is thought to be due in part to the attenuation of Rep toxicity in those cells. In this regard, the placement of the p5 promoter region in a site that is other than its normal position relative to the rep coding region may serve to attenuate production of both Rep 78 and Rep 68 (the long form Rep expression products normally transcribed from the p5 promoter) when the rep coding region is expressed. In light of the fact that some long form Rep products are expressed from the present AAV helper constructs, the relocated AAV p5 promoter region may serve an effector function by virtue of its new position. The Rep 52 and Rep 40 gene products are thought to be produced at normal levels.

In each of the above-described methods, viral helper functions can be expressed in the host cells using methods that are known to those of skill in the art. Particularly, viral helper functions are provided by infection of the host cells with an unrelated helper virus. Helper viruses which will find use with the present systems include the adenoviruses; herpesviruses such as herpes simplex virus types 1 and 2; and vaccinia viruses. Nonviral helpers will also find use herein, such as cell synchronization, using any of various known agents. See, e.g., Buller et al. (1981) *J. Virol.* 40:241–247; McPherson et al. (1985) *Virology* 147:217–222; Schlehofer et al. (1986) *Virology* 152:110–117. As a consequence of the infection of the host cell, the viral helper functions are capable of being expressed to transactivate an AAV helper construct to produce AAV Rep and Cap proteins. In this manner, the Rep proteins serve to excise the recombinant DNA (containing the heterologous nucleotide sequence) from the recombinant AAV vector (or from the host cell genome if the AAV vector has been integrated). The Rep proteins also serve to duplicate the AAV genome. The expressed Cap proteins assemble into capsids, and the recombinant AAV genome is packaged into the capsids. Thus, lytic AAV replication ensues, and the heterologous nucleotide sequence is packaged into viable transducing vectors.

Following expression of the viral helper functions in the host cell and the AAV replication, rAAV virions can be purified from the host cell using a variety of conventional purification methods, such as CsCl gradients. Further, if infection is employed to express the viral helper functions, any residual helper virus can be inactivated, using known methods. For example, adenovirus can be inactivated by heating to temperatures of approximately 60° C. for, e.g., 20 minutes or more, since AAV is extremely heat stable and adenovirus is heat labile.

The resulting rAAV virions containing the heterologous nucleotide sequence of interest can then be used for gene delivery, such as in gene therapy applications, for the production of transgenic animals, in vaccination, ribozyme and antisense therapy, as well as for the delivery of genes in vitro, to a variety of cell types.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

1. Construction of the pAAVlacZ plasmid

An AAV vector carrying the lacZ gene (pAAV-lacZ) was constructed as follows. The AAV coding region of pSub201 (Samulski et al. (1987) *J. Virol* 61:3096–3101), between the XbaI sites, was replaced with EcoRI linkers, resulting in plasmid pAS203. The EcoRI to HindIII fragment of pCMVβ (CLONETECH) was rendered blunt ended and cloned in the Klenow treated EcoRI site of pAS203 to yield pAAV-lacZ.

2. Construction of the pGN1909 plasmid

The AAV helper construct pGN1909 which is capable of expressing the AAV Rep and Cap polypeptide products includes an approximately 4.8 Kb nucleotide stretch comprising an AAV rep and cap coding region and a downstream AAV p5 promoter that are interposed between two FRT sites. The pGN1909 plasmid can be constructed as follows. Referring to FIG. 1, a BglII site is introduced 12 bases 5' of the rep78/68 ATG in the previously-described pAAVAd construct (Samulski et al. (1989) *J. Virol.* 63:3822–3828) resulting in a plasmid called pAAVAd-Bgl. A 50 bp minimum FRT site (Jayaram (1985) *Proc. Natl. Acad. Sci. USA* 82:5875–5879; and O'Gorman (1991) *Science* 251:1351–1355) is then inserted into the BglII site of pAAVAd-Bgl and the resulting FRT-rep-cap fragment lacking the p5 promoter is cloned into the polylinker of pBSIIKS (Stratagene, San Diego, Calif.) to yield a plasmid called pFRTRepCap.

Figure 2:
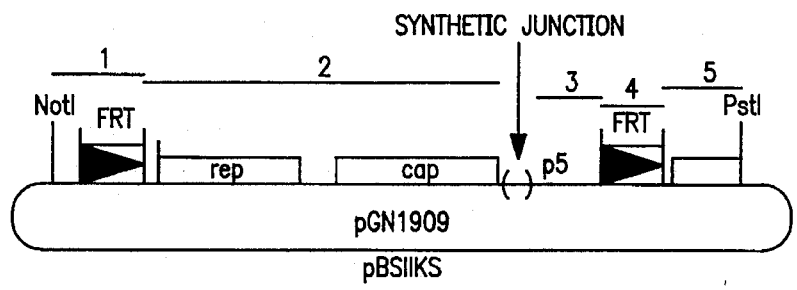
FIG. 2 is a representation of plasmid pGN1909.

In a separate step, a fragment defined by the SpeI and PstI sites of the previously described pIM29+45 plasmid (McCarty et al. (1991) *J. Virol.* 65:2936–2945) which includes an AAV p5 promoter and a portion of the 5' end of the rep gene is subcloned into the polylinker of pBSIIK5 (Stratagene, San Diego, Calif.) between the SpeI and PstI sites. An FRT site is then introduced 12 bp 5' of the rep78/68 ATG, resulting in a plasmid called pGN1901. The SpeI-PstI fragment of pGN1901 is inserted into the XbaI site of the pFRTRepCap plasmid resulting in the pGN1909 plasmid construct. A map of the pGN1909 plasmid is depicted in FIG. 2.

A similar construct can be constructed as follows. The following five nucleotide fragments, arranged in the order given in the 5' to 3' direction are ligated into the polylinker of pBSIIK5 (Stratagene, San Diego, Calif.) between the NotI and the PstI sites: (1) a first nucleotide fragment comprising the 59 bp "minimum" FRT site (Jayaram and O'Gorman, supra) depicted in FIG. 3; (2) a second nucleotide fragment comprising an AAV rep and cap coding region (corresponding to bps 310 through 4484 of the wt AAV genome, Srivastava et al. (1983) *J. Virol.* 45:555–564); (3) a third nucleotide fragment comprising an AAV p5 promoter region (corresponding to bps 145 through 310 of the wt AAV genome, Srivastava et al., supra.); (4) a fourth nucleotide fragment comprising the 76 bp FRT site (Jayaram and O'Gorman, supra) depicted in FIG. 3; and (5) a fifth nucleotide fragment comprising a 184 bp segment of the 5' end of the rep coding region (corresponding to bps 310 through 494 of the wt AAV genome, Srivastava et al., supra).

The five nucleotide sequences are linked together to form a single, contiguous nucleic acid molecule having a synthetic junction interposed between fragments 2 and 3 to facilitate the linkage of those two moieties. The nucleotide sequence of the synthetic junction is as follows: 5'-CTCTAGTGGATCT-3' [SEQ ID NO:1]. Such junctions can be any suitable linker moiety known in the art and are merely used herein to facilitate the assembly of the subject AAV helper construct.

3. Production of AAV vectors

Human 293 cells (Graham et al. (1967) *J. Gen. Virol.* 36:59–72, available from the ATCC under Accession Number CRL1573) are grown in sterile DME/F12 culture medium (without HEPES buffer) that has been supplemented with 10% fetal calf serum (FCS), 1% pen/strep and 1% glutamine (Sigma, St. Louis, Mo.) at 37° C. in 5% $CO_2$. Once the cells are healthy and dividing, they are trypsinized and plated at from $1\times10^6$ to $5\times10^6$ cells per 10 cm cell culture plate. A monolayer confluency of 50 to 75% is achieved when the cells initially attach to the surface of the plate. The volume of medium in each plate is 10 mL. Avoidance of any clumping of the cells and an even distribution in the cell is essential in order to achieve even cell density over all areas of the tissue culture plate (which is important for high rAAV particle yield). The cells are then grown at 37° C. in 5% $CO_2$ to reach 90% confluency over a period of from 24 to 48 hours before transfection.

At 1 to 4 hours prior to transfection, the medium in the tissue culture plates is replaced with fresh DME/F12 culture medium containing 10% FCS, 1% pen/strep and 1% glutamine. 10 µg each of the pAAVlacZ vector and the pGN1909 helper construct (or another suitable helper construct) are added to 1 mL of sterile 300 mM $CaCl_2$, which is then added to 1 mL of sterile 2× HBS solution (formed by mixing 280 mM NaCl, 50 mM HEPES buffer, 1.5 mM $Na_2HPO_4$ and adjusting the pH to 7.1 with 10M NaOH) and immediately mixed by gentle inversion. The resultant mixture is then pipetted immediately into the 10 cm plates of 90% confluent 293 cells (in 10 mL of the above-described culture medium) and swirled to produce a homogeneous solution.

The plates are transferred to a 5% $CO_2$ incubator and cultured at 37° C. for 6 to 8 hours without disturbing. After transfection, the medium is removed from the plates, and the monolayer of cells washed once with sterile Phosphate buffered saline (PBS).

Adenovirus working stock is prepared by diluting a master stock of adenovirus (serotype 2) to a concentration of $10^6$ pfu/mL in DME/F12 plus 10% FCS, 1% pen/strep, 1% glutamine and 25 mM sterile HEPES buffer (pH 7.4). 10 mL of the resulting adenovirus working stock is added to each 10 cm plate and the cells are incubated for approximately 72 hours. When all of the cells show cytopathic effect (CPE), and approximately 30% of the cells are floating, the cells are harvested by gently pipetting the cells to detach them from the plate surface. The cell suspension is collected and centrifuged at 300×g for 2 minutes. The supernatant is aspirated off and the cells are resuspended in 1 mL of sterile Tris buffered saline (TBS, prepared by mixing 100 mL Tris HCL, 150 mM NaCl and adjusted to pH 8.0). The resultant material can be frozen at −80° C., or used immediately to make a freeze/thaw lysate.

The freeze/thaw lysate is prepared by freezing and thawing the TBS:cell suspension 3 times by alternating between a dry ice/ethanol bath (until the cells are completely frozen) and a 37° C. water bath (until completely thawed). Tissue debris is removed by centrifugation at 10,000×g for 10 minutes. The supernatant is collected and transferred to a sterile cryo-vial. The adenovirus is heat inactivated by incubating the freeze/thaw lysate at 56° C. for 1 hour by submersion in a water bath. Any precipitate that forms during the heat inactivation is removed by centrifuging the sample at 10,000×g for 10 minutes. The supernatant containing AAV vector particles is then harvested. The particles can be stored frozen at −70° C.

Transducing vector titers can be determined by infecting 293 cells with a dilution series of the rAAV virions prepared above. After 24 hours, the cells are fixed and stained with X-Gal (Sanes et al. (1986) *EMBO* 5:3133–3142). The titer is calculated by quantifying the number of blue cells.

4. Comparison of AAV helper plasmid efficiency

The efficiency of helper functions provided by the pGN1909 construct was compared against the previously described pAAV/Ad and pIM29+45 AAV helper plasmids (Samulski et al. and McCarty et al., supra). rAAVlacZ virions were prepared by co-transfection of human 293 cells with pAAVlacZ (prepared as described above in Example 1) and one of the three helper plasmids: pGN1909, pAAV/Ad and pIM29+45. The titers of recombinant preparations from the three preparations were determined (as described above in Example 3). The results are depicted in Table 1.

TABLE 1

| AAV Helper Construct | Titers of rAAVlacZ |
| --- | --- |
| pGN1909 | $2.7 \times 10^8$/mL |
| pAAV/Ad | $3.8 \times 10^7$/mL |
| pIM29 + 45 | $1.9 \times 10^7$/mL |

As can be seen by the above results, the titers of recombinant preparations produced using the pGN1909 construct as an AAV helper construct are 5 to 10 fold greater than preparations using either of the two previously described helper plasmids.

Deposits of Strains Useful in Practicing the Invention

A deposit of biologically pure cultures of the following strains was made with the American Type Culture Collection, 12301 Parklawn Drive, Rockville, Md., under the provisions of the Budapest Treaty. The accession number indicated was assigned after successful viability testing, and the requisite fees were paid. Access to said cultures will be available during pendency of the patent application to one determined by the Commissioner to be entitled thereto under 37 CFR 1.14 and 35 USC 122. All restriction on availability of said cultures to the public will be irrevocably removed upon the granting of a patent based upon the application. Moreover, the designated deposits will be maintained for a period of thirty (30) years from the date of deposit, or for five (5) years after the last request for the deposit; or for the enforceable life of the U.S. patent, whichever is longer. Should a culture become nonviable or be inadvertently destroyed, or, in the case of plasmid-containing strains, lose its plasmid, it will be replaced with a viable culture(s) of the same taxonomic description.

These deposits are provided merely as a convenience to those of skill in the art, and are not an admission that a deposit is required. The nucleic acid sequences of these plasmids, as well as the amino sequences of the polypeptides encoded thereby, are controlling in the event of any conflict with the description herein. A license may be required to make, use, or sell the deposited materials, and no such license is hereby granted.

| Strain | Deposit Date | ATCC No. |
| --- | --- | --- |
| pGN1909 | July 20, 1995 | 69871 |

I claim:

1. A nucleic acid molecule encoding AAV helper functions, said molecule comprising:
   an AAV rep coding region;
   an AAV cap coding region; and
   a first nucleotide sequence comprising an AAV p5 promoter region, said first nucleotide sequence arranged in the molecule such that the p5 promoter region is situated 3' relative to the rep coding region.

2. The nucleic acid molecule of claim 1, wherein the first nucleotide sequence comprises base pairs (bps) 145 through 309 as depicted in FIG. 4 (SEQ ID NO:4) of the wild-type AAV serotype 2 genome, or functional equivalents thereof.

3. The nucleic acid molecule of claim 1, wherein the first nucleotide sequence comprises bps 145 through 494 as depicted in FIG. 4 (SEQ ID NO:4) of the wild-type AAV serotype 2 genome, or functional equivalents thereof.

4. The nucleic acid molecule of claim 1, further including a second nucleotide sequence comprising a Flip Recombination Target (FRT) site or a functional equivalent thereof, said second nucleotide sequence positioned such that the molecule comprises, in the order given in the 5' to 3' direction, the second nucleotide sequence, an AAV rep coding region, an AAV cap coding region, and a nucleotide sequence comprising an AAV p5 promoter region.

5. The nucleic acid molecule of claim 1, further comprising a 5' and a 3' flanking nucleotide sequence, wherein each said flanking sequence comprises an FRT site or a functional equivalent thereof, and further wherein the AAV rep coding region, the AAV cap coding region, and the nucleotide sequence comprising the AAV p5 promoter region are interposed between said flanking nucleotide sequences.

6. The nucleic acid molecule of claim 1, further comprising an intervening nucleotide sequence, wherein the molecule comprises, in the order given in the 5' to 3' direction, an AAV rep coding region, an AAV cap coding region, the intervening nucleotide sequence, and a nucleotide sequence comprising an AAV p5 promoter region.

7. An AAV helper construct comprising the nucleic acid molecule of claim 1.

8. The nucleic acid molecule of claim 3, further including a second nucleotide sequence comprising an FRT site or a functional equivalent thereof, said second nucleotide sequence positioned such that the molecule comprises, in the order given in the 5' to 3' direction, the second nucleotide sequence, an AAV rep coding region, an AAV cap coding region, and a nucleotide sequence comprising an AAV p5 promoter region.

9. The nucleic acid molecule of claim 3, further comprising a 5' and a 3' flanking nucleotide sequence, wherein each said flanking sequence comprises an FRT site or a functional equivalent thereof, and further wherein the AAV rep coding region, the AAV cap coding region, and the nucleotide sequence comprising the AAV p5 promoter region are interposed between said flanking nucleotide sequences.

10. The nucleic acid molecule of claim 3, wherein the nucleotide sequence that comprises the AAV p5 promoter region further comprises an FRT site inserted therein such that said FRT site is situated immediately 3' of the AAV p5 promoter region.

11. The nucleic acid molecule of claim 10, further including a second nucleotide sequence comprising an FRT site or a functional equivalent thereof, wherein the molecule comprises, in the order given in the 5' to 3' direction, the second nucleotide sequence, an AAV rep coding region, an AAV cap coding region, and a nucleotide sequence comprising an AAV p5 promoter region and having an FRT site situated immediately 3' of the AAV p5 promoter region.

12. An AAV helper construct comprising the nucleic acid molecule of claim 11.

13. The nucleic acid molecule of claim 6, wherein the intervening nucleotide sequence has a length sufficient to prevent the packaging in an AAV virion of a molecule produced by a recombination of said nucleic acid molecule with AAV ITRs during recombinant AAV virion production.

14. An AAV helper construct comprising the nucleic acid molecule of claim 13.

15. The AAV helper construct of claim 7, wherein said construct comprises a plasmid.

16. The construct of claim 7, further comprising a selectable genetic marker.

17. An AAV packaging cell prepared by transfecting a suitable host cell with the AAV helper construct of claim 7.

18. A method of producing recombinant AAV virions, comprising the steps:
   (a) introducing an AAV vector into a host cell;
   (b) introducing the AAV helper construct of claim 7 into the host cell such that the construct provides essential AAV Rep and Cap polypeptides;
   (c) expressing viral helper functions in the host cell; and
   (d) culturing the cell to produce recombinant AAV virions.

19. The AAV helper construct of claim 12, wherein said construct comprises a plasmid.

20. The AAV helper construct of claim 19, wherein said construct comprises the plasmid pGN1909 (ATCC Accession Number 69871).

21. The construct of claim 20, further comprising a selectable genetic marker.

22. An AAV packaging cell prepared by transfecting a suitable host cell with the AAV helper construct of claim 20.

23. A method of producing recombinant AAV virions, comprising the steps:
   (a) introducing an AAV vector into a host cell;
   (b) introducing the AAV helper construct of claim 20 into the host cell such that the construct provides essential AAV Rep and Cap polypeptides;
   (c) expressing viral helper functions in the host cell; and
   (d) culturing the cell to produce recombinant AAV virions.

24. The AAV helper construct of claim 14, wherein said construct comprises a plasmid.

25. The construct of claim 14, further comprising a selectable genetic marker.

26. An AAV packaging cell prepared by transfecting a suitable host cell with the AAV helper construct of claim 14.

27. A method of producing recombinant AAV virions, comprising the steps:
(a) introducing an AAV vector into a host cell;
(b) introducing the AAV helper construct of claim 14 into the host cell such that the construct provides essential AAV Rep and Cap polypeptides;
(c) expressing viral helper functions in the host cell; and
(d) culturing the cell to produce recombinant AAV virions.

28. The construct of claim 16, wherein the selectable genetic marker comprises an antibiotic resistance gene.

29. The construct of claim 21, wherein the selectable genetic marker comprises an antibiotic resistance gene.

30. The construct of claim 25, wherein the selectable genetic marker comprises an antibiotic resistance gene.

31. An AAV producer cell capable of producing recombinant AAV virions when viral helper functions are expressed therein, said producer cell comprising the packaging cell of claim 22 that has been transfected with an AAV vector.

32. An AAV producer cell capable of producing recombinant AAV virions when viral helper functions are expressed therein, said producer cell comprising the packaging cell of claim 26 that hag been transfected with an AAV vector.

33. The method of claim 18, wherein the expression of viral helper functions is provided by infecting the host cell with a virus selected from the group consisting of adenovirus, herpesvirus and vaccinia virus.

34. The method of claim 23, wherein the expression of viral helper functions is provided by infecting the host cell with a virus selected from the group consisting of adenovirus, herpesvirus and vaccinia virus.

35. The method of claim 27, wherein the expression of viral helper functions is provided by infecting the host cell with a virus selected from the group consisting of adenovirus, herpesvirus and vaccinia virus.

* * * * *